United States Patent [19]

David

[11] 4,310,955
[45] Jan. 19, 1982

[54] BLOOD ELEMENT SEPARATION APPARATUS

[76] Inventor: Henry B. David, 5708 Oakdale Ave., Woodland Hills, Calif. 91367

[21] Appl. No.: 108,834

[22] Filed: Dec. 31, 1979

[51] Int. Cl.³ .................. B65D 77/10; A44B 21/00
[52] U.S. Cl. .................. 24/248 B; 24/30.5 R; 248/316 B; 248/95
[58] Field of Search .................. 24/248 B, 30.5 R; 248/95, 316 B

[56] References Cited

U.S. PATENT DOCUMENTS

| | | | |
|---|---|---|---|
| 207,469 | 8/1878 | Wolf | 24/248 B |
| 1,404,436 | 1/1922 | Giroux | 248/316 B |
| 1,482,662 | 2/1924 | Sheppard | 24/30.5 R |
| 1,691,155 | 11/1928 | Howell | 248/316 B |
| 2,031,508 | 2/1936 | Scott | 248/316 B |
| 2,337,580 | 12/1943 | Webster | 24/30.5 R |
| 2,377,953 | 6/1945 | Matton | 24/248 B |
| 2,425,260 | 8/1947 | Mayer | 248/95 |

*Primary Examiner*—Victor N. Sakran
*Attorney, Agent, or Firm*—Michael A. Painter

[57] ABSTRACT

A clamping apparatus for mechanically separating cellular elements suspended in whole blood solutions. After subjecting sealed packets of whole blood to centrifugal forces which will cause isolation of red and white blood cells, the packet is inserted within the present invention apparatus at the interface of the isolated red and white cells. A pair of parallel, spaced clamping surfaces are brought into juxtaposition with the sides of the blood packet along the cell interface causing the interior surface of the blood packet to mechanically isolate the cells along the edges of the opposed surfaces. A pair of securing arms are urged against a resilient force secured across the clamping surfaces to maintain a substantially constant force along the entire portion of the blood packet in contact with the clamping surfaces.

8 Claims, 5 Drawing Figures

BLOOD ELEMENT SEPARATION APPARATUS

BACKGROUND OF THE INVENTION

1. Field of the Invention

The present invention generally relates to blood separation apparatus and, more particularly, to those apparatus adapted to utilize containers of whole blood fabricated of vinyl or related resilient material.

2. Prior Art

It has long been known that substantial benefits can occur through the use of various elements of whole blood. The separation of plasma, white cells, red cells, platelets, etc., from a whole blood solution provides a variety of uses which are well known throughout the field of medicine. The methods used by the devices taught by the prior art are not precise in that substantial quantities of the elements sought to be obtained are lost as a result of the inability of sufficiently isolate and subsequently separate the blood elements. A conventional method taught by the prior art utilizes a centrifuge to temporarily isolate the elements utilizing the elements quantitative difference in mass. For example, subjecting a packet of whole blood to centrifugal force will isolate the red cells from the remaining suspended elements as a result of their greater mass. After separation, gravitational forces are used to pour off the red cells. Inefficiency and problems inherent in this method arise from the conventional use of the vinyl or other flexible containers used to store blood solutions. The surface tension between the blood solution and the surface of vinyl or other flexible material used in the container results in an effect referred to as an hourglass effect whereby the flow of liquid from the volume of fluid not in contact with the interior surface of the container is faster than that along the surface itself. Where the red cells are drained off through the use of gravity, any white cells which may be disposed atop the interior volume of the red cell solution will be lost since the flow at that point will be greater than the velocity of the fluid along the container's interior surface.

The present invention substantially resolves those problems inherent in the methods and devices taught by the prior art. After separating the red and white cells through the use of conventional centrifugal equipment, the packet is inserted between a pair of clamping surfaces which are disposed along the interface of the red and white cells. Since vinyl or other flexible materials can have varying thicknesses, the clamping surfaces are maintained in a closed condition through the use of a resilient force which will automatically adjust to the thickness of the container. After the suspended cellular materials are mechanically separated through use of the container walls themselves, the white cells can be drained off from the packets without any loss thereof.

SUMMARY OF THE INVENTION

The present invention constitutes a mechanical separation apparatus which can be used to separate elements which are suspended in a fluid solution and which have been temporarily isolated through the use of conventional centrifuges or other suitable methods. Although it is clear that the use of the present invention can be used for mechanical separation and isolation of any tupe of elements which are suspended in a liquid solution, the preferred use of the present invention relates to the isolation, separation and recovery of white blood cells from whole blood. It is well known in the field of medical research that the isolation of blood components is an important and, in fact, necessary procedure. Whole blood is comprised of red cells, white cells, platelets, plasma, etc. In order to isolate blood cells from the remaining blood solution, the use of conventional centrifugal apparatus is well known. Since red blood cells differ in mass from that of white blood cells, they can be isolated in solution by the application of centrifugal force to the containers within which the whole blood solution is maintained. Typical containers for whole blood are fabricated of vinyl or other flexible material which can be easily stored. The packets are typically square or rectangular in shape and are sealed along the outer edges thereof. A tube or like structure provides access to the interior cavity of the vinyl packet in order to provide for filling and otherwise provides access to the blood being maintained within the container.

As stated hereinabove, one of the most difficult problems in blood research has been the separation of white cells from red cells after the have been isolated in solutions through the use of centrifuges. The present invention substantially increases the yield which has been obtained with the procedures and apparatus described in the prior art.

Following the centifugal isolation of red and white cells within the blood solution stored within the vinyl packet, separation is accomplished through the use of the present invention. The present invention comprises a pair of planar surfaces each having an edge in parallel relationship to each other and adapted to be brought in contact along the full extent of those edges. The planar surfaces are pivotable on opposite sides thereof whereby each edge moves about the pivotal coupling at a fixed radius. A pair of lever arms are coupled on opposite sides of one of the planar surfaces, each lever arm being resiliently coupled on opposite sides of the second planar surface.

After a container of blood solution has been subjected to centrifugal forces whereby the red and white blood cells have been isolated, the container is inserted between the edges of the planar surfaces and the lever arms rotated to oppose the resilient coupling. The edges of both planar surfaces will bear against the flexible container inserted therebetween causing the isolation of the red and white cells to be maintained in a manner which will preclude passage of any fluid across the locked interface. Once the container is maintained in a locked position, the white cells can be drained off through the use of an access tube integral with the blood solution container.

It is therefore an object of the present invention to provide an improved method and apparatus for separating red and white cells from a blood solution.

It is another object of the present invention to provide a blood solution separation apparatus which operates independent of the thickness of the solution container.

It is yet another object of the present invention to provide a blood solution separation apparatus which will inhibit contamination of isolated red and white cells during the separation thereof.

It is still yet another object of the present invention to provide a blood solution separation apparatus which is simple and inexpensive to fabricate.

The novel features which are believed to be characteristic of the invention, both as to its organization and method of operation, together with further objectives and advantages thereof, will be better understood from the following description considered in connection with the accompanying drawing in which a presently preferred embodiment of the invention is illustrated by way of example. It is to be expressly understood, however, that the drawing is for the purpose of illustration and description only and is not intended as a definition of the limits of the invention.

DESCRIPTION OF THE PRESENTLY PREFERRED EMBODIMENT

Figure 1:
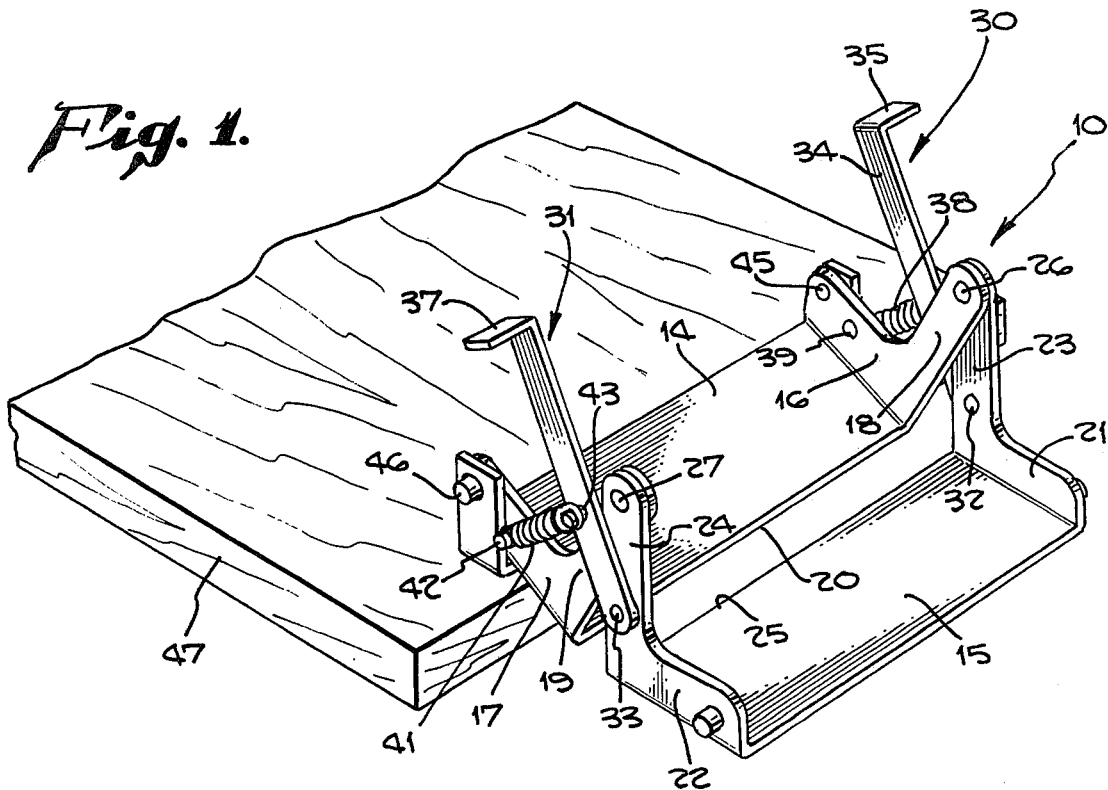
FIG. 1 is a perspective view of the present invention blood solution separation apparatus.
Figure 5:
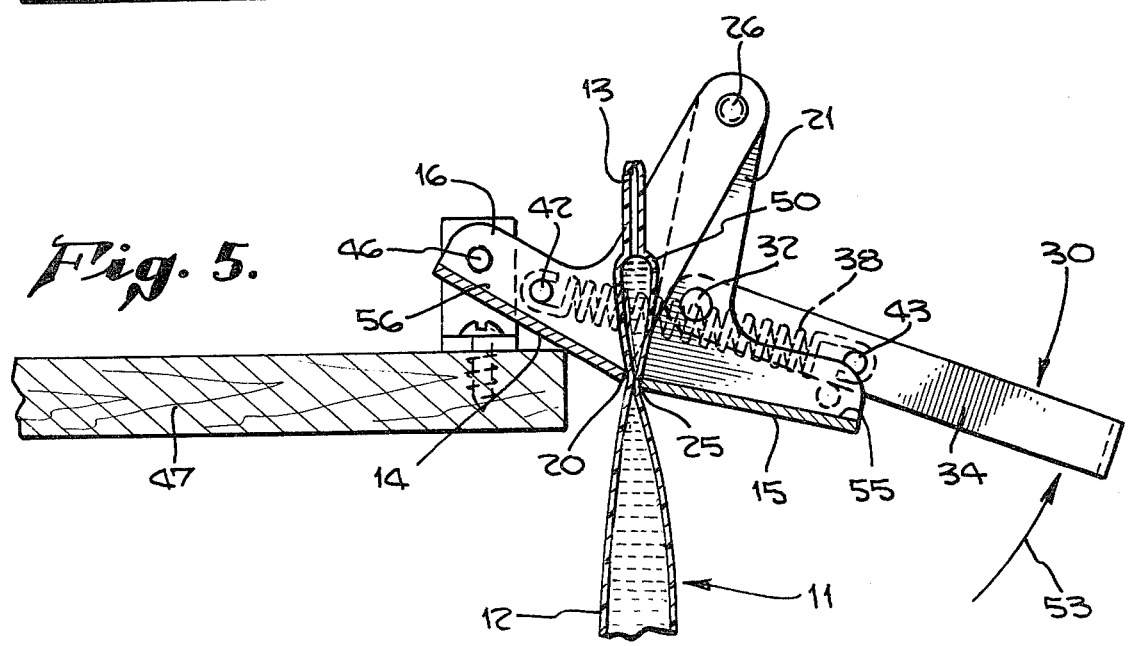
FIG. 5 is a cross-sectional view of the blood solution separation apparatus and the clamped blood solution packet taken through line 5—5 of FIG. 4.

An understanding of the present invention can be best gained by reference to FIG. 1 wherein a perspective view of the present invention blood solution separation apparatus is shown therein generally designated by the reference numeral 10. The present invention 10 is used to separate isolated red and white blood cells of a blood solution stored in conventional vinyl packets. As shown in FIG. 5, a typical vinyl packet 11 used to store blood solutions comprises a pair of side walls 12 which are typically rectangular and which when joined along the periphery thereof to form a cavity within which blood solution is stored. An access tube 13 is integral with one of the side walls to provide an input and output source for the fluid stored within the packet 11. One of the difficulties associated with conventional packets 11 is the variation in the thickness of the side walls 12. As will be discussed in detail hereinbelow, the present invention provides for the separation of the isolated elements by applying a resilient force against the exterior of side walls 12 to create a barrier between the isolated elements during the separation process.

Figure 2:
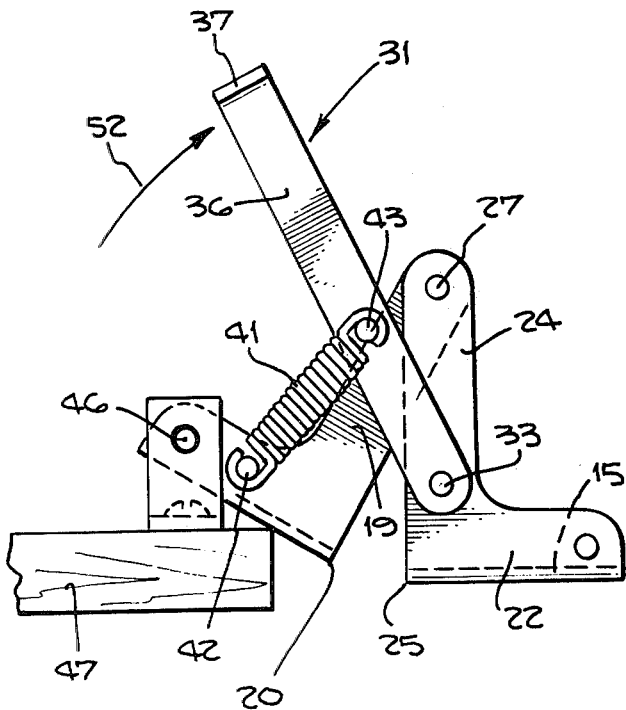
FIG. 2 is a side elevation view of the present invention blood separation apparatus showing the locking surfaces in an open position.
Figure 3:
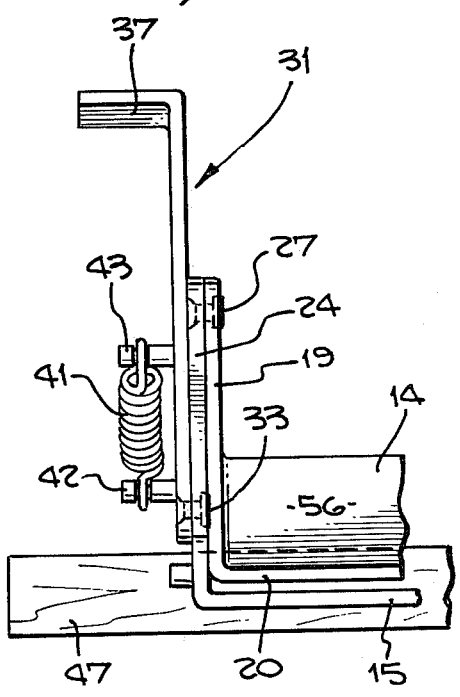
FIG. 3 is a partial, front elevation view of the present invention apparatus as shown in FIG. 1 taken along the plane of the front planar surface.

Referring to FIGS. 1, 2 and 3, a pair of planar surfaces 14 and 15 are used to apply a resilient force against the exterior of the side walls 12 of packet 11. Surface 14 is substantially rectangular in shape and is fabricated from a sturdy material which will not deform during the separation process. The narrow ends of surface 14 depend into flanges 16 and 17 along opposite edges thereof, flanges 16 and 17 being parallel to each other. Flanges 16 and 17 are substantially L-shaped, the extended portions 18 and 19 of flanges 16 and 17 respectively are contiguous with edge 20. Surface 15 is substantially rectangular, the narrow edges thereof being extended perpendicularly into flanges 21 and 22 in the same manner as flanges 16 and 17 depend upwardly from surface 14. Flanges 21 and 22 are perpendicular to surface 15. Flanges 21 and 22 have extended portions 23 and 24, each having an edge contiguous with edge 25.

Extensions 18 and 23 of flanges 16 and 21, respectively, are pivotally coupled to one another at the termini thereof, pivotal coupling 26 maintaining flanges 16 and 21 adjacent one another while permitting said flanges to rotate with respect to each other about pivotal coupling 26. In a like manner, extensions 19 and 24 of flanges 17 and 22 are pivotally coupled to one another at the termini thereof, pivotal coupling 27 maintaining the adjacent relationship of flanges 17 and 22 while permitting relative rotation thereof about pivotal coupling 27.

Edges 20 and 25 of surfaces 14 and 15, respectively, are in parallel relationship to one another between the interval defined by flanges 17 and 18. When surface 15 is fully rotated in a clockwise direction as shown in FIG. 1, edges 20 and 25 will be in full contact with one another along the full extent illustrated. In order to permit edges 20 and 25 to be locked in an adjacent position, independent lever arms 30 and 31 are pivotally coupled to flanges 21 and 22 by conventional rotating couplings 32 and 33 respectively. Lever arms 30 and 31 are rotatably coupled to flanges 21 and 22 respectively in planar opposition to the couplings of flanges 16 and 17 to 21 and 22, respectively. Lever arm 30 comprises an extension arm 34 which is parallel to and adjacent flange 21, extension arm 34 depending into a locking handle 35 which will facilitate movement of lever arm 30 about rotatable coupling 32. In a like manner, lever arm 31 comprises extension arm 36 which is parallel to and adjacent flange 22, extension arm 36 depending into locking handle 37. A resilient member in the form of a helical spring 38 is joined at either end thereof to couplings 39 and 40 on flange 16 and extension arm 34, respectively. In a like manner, a resilient element in the form of helical spring 41 is secured between couplings 42 and 43 which are secured upon flange 17 and extension arm 31, respectively. As can be best seen in FIG. 1, couplings 39 and 42 are secured upon flanges 16 and 17, respectively, substantially intermediate edge 20 and the parallel, spaced edge of surface 14. Couplings 40 and 43 are secured upon extension arms 34 and 36 substantially intermediate rorating couplings 32 and 33 and the opposing locking handles 35 and 37, respectively.

The present invention blood solution separation apparatus 10 is rotatably coupled to a fixed surface 47 through the use of pivotal couplings 45 and 46. As shown in FIG. 1, pivotal couplings 45 and 46 are secured to a fixed surface 47 and are coupled to flanges 16 and 17, respectively, along the edge of surface 14 substantially opposite edge 20.

Figure 4:
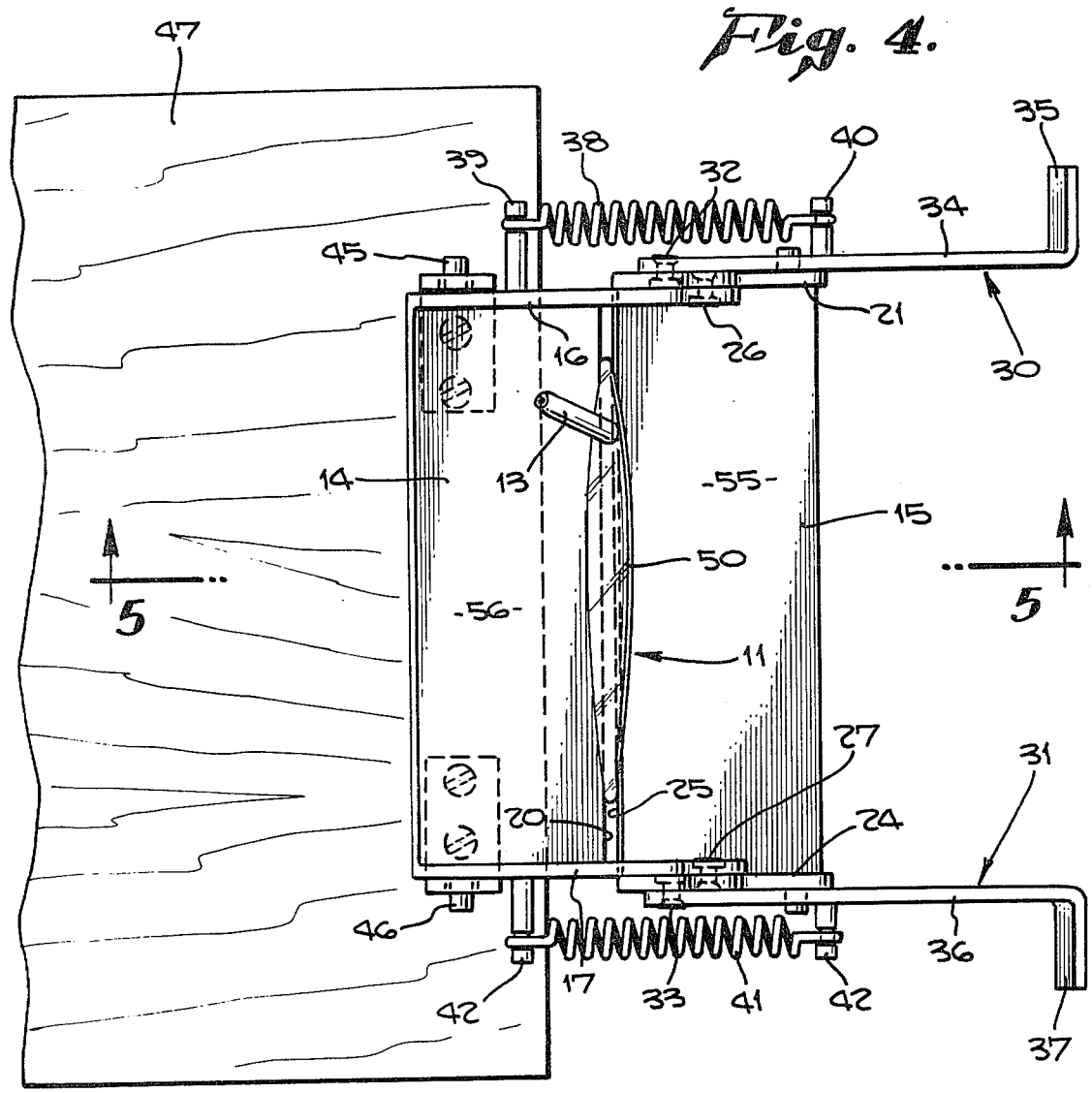
FIG. 4 is a top plan view of the present invention blood solution separation apparatus shown in locked position with a blood solution packet clamped therein.

The use of the present invention can be best seen by reference to FIGS. 2, 4 and 5. In operation, the blood solution contained in a vinyl packet 11 is initially prepared by subjecting the packet to centrifugal forces whereby heavier elements in a blood solution are disposed in the portion of the packet opposite access tube 13. Through use of procedures which are well known to persons having skill in the art, white cells and red cells of a whole blood solution can be temporarily isolated through the use of conventional centrifuges whereby the white cells can be isolated within the portion of packet 11 shown in FIG. 5 by the reference numeral 50. The heavier red cells are temporarily isolated in the portion of the interior cavity designated in FIG. 5 by the reference numeral 51. A special interface will temporarily be maintained between the white cells 50 and red cells 51. After completing the initial step in the isolation and separation procedure, the vinyl packet 11 is disposed between edges 20 and 25, edges 20 and 25 being aligned with the interface separating white cells 50 and red cells 51. As shown in FIG. 2, the interval between edges 20 and 25 can be opened for access by the counterclockwise rotation of planar surface 15 about pivotal coupling 27. Vinyl packet 11 is inserted between edges 20 and 25 along the temporary interface between red cells 51 and white cells 50. Planar surface 15 is then rotated clockwise until vinyl packet 11 is disposed adjacent edges 20 and 25 after which lever arms 30 and 31 are rotated clockwise as shown in FIG. 2 by the reference numeral 52. By rotating lever arms 30 and 31 about pivotal couplings 32 and 33 as shown in FIGS. 4 and 5, a substantially equal force will be imposed by edges 20 and 25 along the entire spacial interface isolating white cells 50 and red cells 51. Since the thickness of side walls 12 can vary, the independent application of force between the outer extremeties of edges 20 and 25 will uniformly force the interior of side walls 12 against one another in a manner which is independent of the thickness of side walls 12. The resilient forces imposed by helical springs 48 and 41 will insure that the interface between white cells 50 and red cells 51 is maintained in tact until the white cells 50 have been separated from the remainder of the fluid stored within vinyl packet 11.

As can be best seen in FIG. 5, the angle between the planar portions of planar surfaces 14 and 15 is less than 180°. By providing an off-set angle between planar surfaces 14 and 15, the opposing forced imposes upon vinyl packet 11 are restricted to a narrower band across side walls 12. In addition, an operator viewing the inserted vinyl packet will have improved visual observation of the portion of packet 11 from which white cells 50 are to be separated thereby improving the total process.

To separate white cells 50, the present invention solution separation apparatus is rotated counterclockwise about pivotal couplings 45 and 46 as shown by the directional arrow indicated by the reference numeral 53. By severing access tube 13, the white cells 50 disposed in the solution isolated from red cells 51 can be syphoned off by graivitational forces. It can therefore be seen that the present invention provides an improved apparatus for the separation of isolated elements in a blood solution in a manner which is simple and inexpensive to fabricate.

I claim:
1. A fluid element separation apparatus comprising:
  (a) first and second planar separation members, each including a planar surface having a clamping edge thereon, said edges being in parallel relation to each other and are adapted to be placed adjacent one another along the full extent of said clamping edges, said planar separation members being pivotally coupled to one another whereby said clamping edges can be separated in parallel, spaced relation to one another;
  (b) first and second locking members, each being rotatably coupled to said first planar separation member on opposite sides of the clamping edge of said first planar separation members; and
  (c) first and second resilient means for maintaining said clamping edges adjacent one another, said first resilient member being coupled intermediate said first locking member and said second planar separation member, said second resilient member being coupled intermediate said second locking member and said second planar separation member whereby the resilient forces imposed by said clamping edges are responsive to the thickness of any object disposed therebetween.

2. A fluid element separation apparatus as defined in claim 1 wherein the angle between the planar surfaces of said first and second planar separation member is less than 180° of arc when the clamping edges of said first and second planar separation members are adjacent one another.

3. A fluid element separation apparatus as defined in claim 1 wherein said first and second resilient means comprise helical springs.

4. A fluid element separation apparatus as defined in claim 1 including a fixed surface, said second planar separation member being pivotally coupled to said fixed surface.

5. A fluid element separation apparatus for use with storage containers having flexible side walls of varying thicknesses, said fluid element separation apparatus comprising:
  (a) first and second planar separation members each including a planar surface having a clamping edge along one side thereof and a pair of upwardly depending, parallel flanges on opposite sides of said clamping edge, said flanges being perpendicular to said planar surface and said clamping edge;
  (b) rotation means for pivotally coupling said first and second separation members to one another at respective pairs of the flanges and adapting said clamping edges to be placed adjacent one another and be separated in parallel spaced relation to one another;
  (c) first and second locking members, each being rotatably coupled to one of the flanges of said first planar separation member, said first and second locking members being aligned with one another; and
  (d) first and second resilient means for maintaining said clamping edges adjacent one another, said first resilient member being coupled intermediate said first locking member and an aligned flange of said second planar separation member, said second resilient member being coupled intermediate said second locking member and an aligned flange of said second planar separation member whereby independent resilient forces are imposed by the clamping edges on the side walls of the storage container responsive to the thickness of the side walls.

6. A fluid element separation apparatus as defined in claim 5 wherein the angle between the planar surfaces of said first and second planar separation member is less than 180° of arc when the clamping edges of said first and second planar separation members are adjacent one another.

7. A fluid element separation apparatus as defined in claim 5 wherein said first and second resilient members comprise helical springs.

8. A fluid element separation apparatus as defined in claim 5 including a fixed surface, the opposed flanges of said second planar separation member being pivotally coupled to the fixed surface.

* * * * *